US008075764B2

(12) United States Patent
Yang et al.

(10) Patent No.: US 8,075,764 B2
(45) Date of Patent: Dec. 13, 2011

(54) APPARATUS FOR REMOVING BUOYANT POLLUTANTS FROM POLLUTED COOLANT

(75) Inventors: Ming-Lu Yang, Taipei Hsien (TW); Wei-Guo Yang, Shenzhen City, Guangdong Province (CN); Zheng-Hong Chi, Shenzhen City, Guangdong Province (CN); Yu-Jun Wang, Shenzhen City, Guangdong Province (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 856 days.

(21) Appl. No.: 12/126,984

(22) Filed: May 26, 2008

(65) Prior Publication Data

US 2009/0145824 A1 Jun. 11, 2009

(30) Foreign Application Priority Data

Dec. 7, 2007 (CN) .......................... 2007 1 0202925

(51) Int. Cl.
*B01D 21/00* (2006.01)

(52) U.S. Cl. ..................... 210/97; 210/167.01; 210/206; 210/242.3; 210/760

(58) Field of Classification Search .................... 210/97, 210/167.01, 201, 202, 206, 242.1, 242.3, 210/416.1, 760
See application file for complete search history.

(56) References Cited

U.S. PATENT DOCUMENTS

| 2,578,040 | A | * | 12/1951 | Booth et al. | 508/111 |
| 3,831,756 | A | * | 8/1974 | Bhuta et al. | 210/109 |
| 5,601,705 | A | * | 2/1997 | Glasgow | 210/104 |
| 6,027,658 | A | * | 2/2000 | Soble et al. | 210/801 |
| 6,790,368 | B1 | * | 9/2004 | Vachon et al. | 210/747.1 |
| 6,966,443 | B1 | * | 11/2005 | Ridge | 210/446 |
| 7,445,719 | B2 | * | 11/2008 | Lundback et al. | 210/741 |
| 7,740,757 | B2 | * | 6/2010 | Yang et al. | 210/171 |

* cited by examiner

*Primary Examiner* — Fred Prince
(74) *Attorney, Agent, or Firm* — Altis Law Group, Inc.

(57) ABSTRACT

An exemplary apparatus (100), for removing buoyant pollutants from a polluted coolant, includes a collecting device (10) and a removing device (20). The collecting device includes a pollutant collecting structure (11) and a bi-directional pump (12). The pollutant collecting structure includes a hollow tub (112) and a collecting module (113) slidable relative to the hollow tub. The bi-directional pump communicates with the hollow tub and the removing device. The removing device includes a filter (21) and a pollutant removing structure (22) disposed on the filter. The filter includes a filtrating unit (211). The filtrating unit is partitioned into a first cavity (2132) and a second cavity (2133) by a partition sheet (213). The partitioning board defines a communicating gap (2131) for the first cavity and the second cavity to communicate with each other. The pollutant removing structure includes a removing member (221) for removing the buoyant pollutants out of the filter.

18 Claims, 8 Drawing Sheets

APPARATUS FOR REMOVING BUOYANT POLLUTANTS FROM POLLUTED COOLANT

CROSS-REFERENCE TO RELATED APPLICATIONS

This application is related to two U.S. patent applications, which are co-pending U.S. patent application Ser. No. 12/107,777 Apr. 23, 2008, entitled "APPARATUS FOR REMOVING BUOYANT POLLUTANTS", and U.S. patent application Ser. No. 12/126,983 filed on May 26, 2008 and issued on Jun. 22, 2010 with issue No. 7,740,757, entitled "APPARATUS FOR REMOVING BUOYANT POLLUTANTS", wherein the inventor of both related applications is Ming-Lu Yang et al. Both of such related applications have the same assignee as the present application. The disclosures of the above identified related applications are incorporated herein by reference.

BACKGROUND OF THE INVENTION

1. Field of the Invention

The present invention generally relates to apparatuses for removing buoyant pollutants, and more particularly, to an apparatus for removing buoyant pollutants from a polluted coolant.

2. Discussion of the Related Art

In order to prevent overheating of cutting tools, a coolant is generally applied to the cutting tool to cool it. However, when using the cutting tool, pollutants, such as oil, and debris, such as dust and other particles, may contaminate the coolant in a coolant tank. The oil generally floats atop the coolant. Some of the debris will mix with the coolant, some debris will sink to the bottom of the coolant, and some debris will mix with the oil and float atop the coolant. Because the majority of coolants for cutting tools are viscous, most of the debris will mix with the oil and float atop the coolant.

The coolant tank for receiving the coolant is generally badly ventilated. In badly ventilated environment, contamination of the coolant will increase and because most of the pollutants are buoyant this creates a haven for micro-organisms and the micro-organisms further contaminate the coolant. When the contaminated coolant is applied to the cutting tool, the cutting tool erodes and deteriorates, resulting in poor quality work-pieces machined by the cutting tool. In addition, the contaminated coolant may also be a health hazard. Therefore, the coolant must be changed periodically to prevent contamination. Changing the coolant increases costs and takes time, thus decreasing the work efficiency.

In order to extend the usage life of the coolant, the buoyant pollutants such as oil and debris floating atop a body of the coolant should be removed by an apparatus. There are mainly four typical kinds of apparatuses for removing buoyant pollutants from the coolant: a rubber-strip-type apparatus, a metal-strip-type apparatus, a swob-type apparatus, and a whirlpool-type apparatus. The rubber-strip-type apparatus includes a rubber strip for absorbing buoyant pollutants. The rubber-strip-type apparatus is stable for removing buoyant pollutants, but the usage life of the rubber strip is short and the efficiency is relatively low. The metal-strip-type apparatus includes a metallic strip for removing buoyant pollutants. The usage life of the metallic strip is relatively long, but the efficiency of the metallic strip is also relatively low. The swob-type apparatus includes a swob for absorbing buoyant pollutants. The efficiency of the swob-type apparatus is high, but the swob is easily damaged when there are a lot of impurities in the coolant. The whirlpool-type apparatus has a high efficiency, and also has a relative long usage life, but the whirlpool-type apparatus is easily clogged by impurities collected from the coolant.

Therefore, an apparatus that is less likely to be clogged by impurities and has high efficiency for removing buoyant pollutants, and to be stable over the long term, is desired.

SUMMARY

An apparatus, for removing buoyant pollutants from a polluted coolant, includes a collecting device and a removing device. The collecting device includes a pollutant collecting structure and a bi-directional pump. The pollutant collecting structure includes a hollow tub and a collecting module. The collecting module is slidable relative to the hollow tub. The bi-directional pump communicates with the hollow tub and the removing device. The removing device includes a filter and a pollutant removing structure disposed on the filter. The filter includes a filtrating unit for removing the buoyant pollutants from the polluted coolant. The filtrating unit is partitioned into a first cavity and a second cavity by a partition sheet. The partition sheet defines a communicating gap for the first cavity and the second cavity to communicate with each other. The pollutant removing structure includes a removing member for removing the buoyant pollutants out of the filter.

Other advantages and novel features will become more apparent from the following detailed description when taken in conjunction with the accompanying drawings.

BRIEF DESCRIPTION OF THE DRAWINGS

The components in the drawings are not necessarily drawn to scale, the emphasis instead being placed upon clearly illustrating the principles of the present apparatus for removing buoyant pollutants from polluted coolant. Moreover, in the drawings, like reference numerals designate corresponding parts throughout the several views, and all the views are schematic.

DETAILED DESCRIPTION OF THE EMBODIMENTS

Reference will now be made to the drawings to describe preferred embodiments of the present apparatus in detail.

Figure 1:
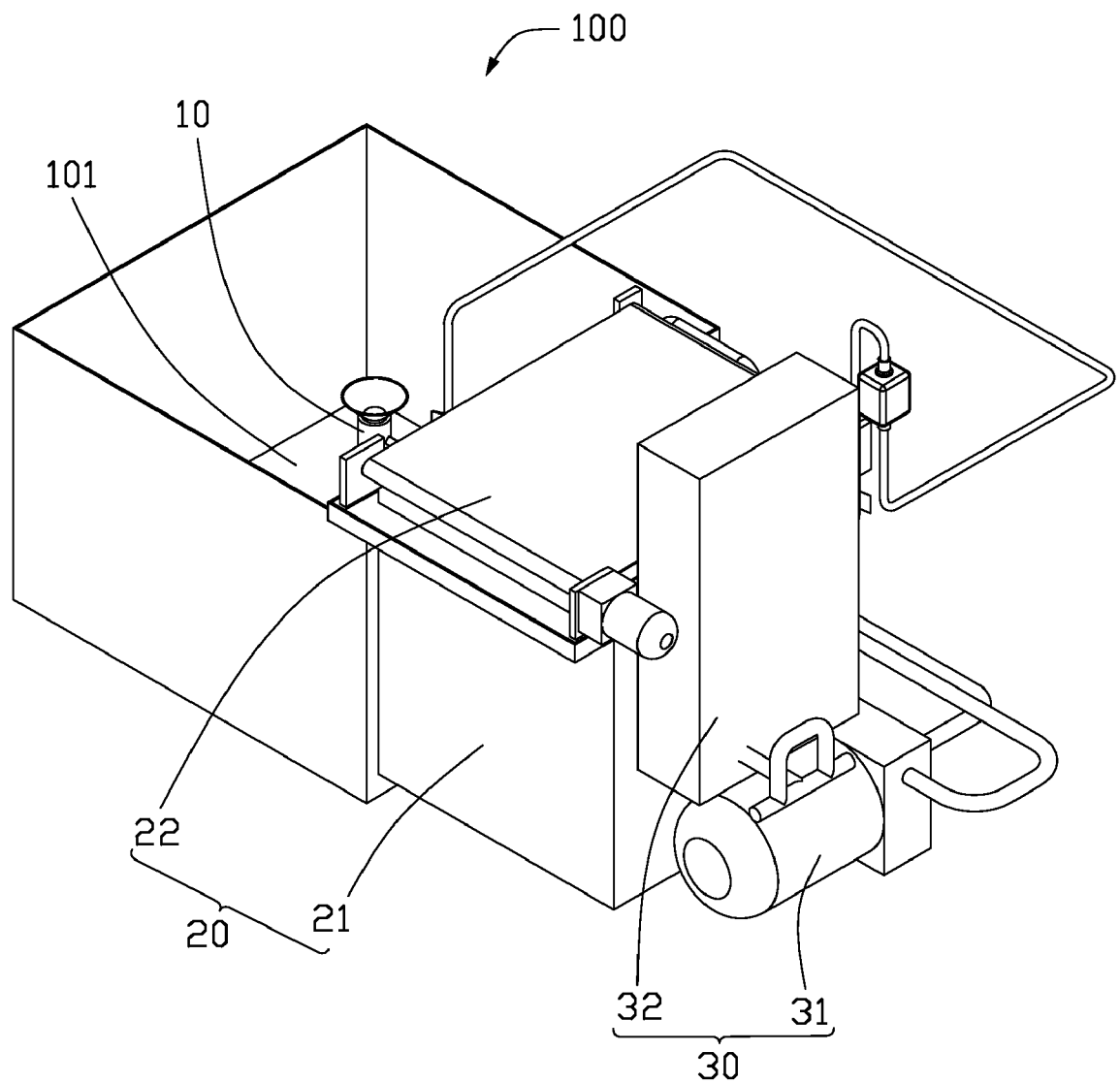
FIG. 1 is an assembled, isometric view of an apparatus for removing buoyant pollutants from polluted coolant in accordance with an exemplary embodiment of the present invention.

Referring to FIG. 1, an apparatus 100 for removing buoyant pollutants such as debris and oil floating atop a body of a polluted coolant in accordance with an exemplary embodiment is shown. The apparatus 100 includes a collecting device 10, a removing device 20, and a bactericidal device 30. The collecting device 10 is configured for pumping a liquid having buoyant pollutants, and polluted coolant from a coolant tank 101 of a machine (not shown) into the removing device 20. The removing device 20 is configured for removing the buoyant pollutants from the coolant so that the coolant can be filtrated. The bactericidal device 30 is configured for killing micro-organisms in the polluted coolant.

Figure 2:
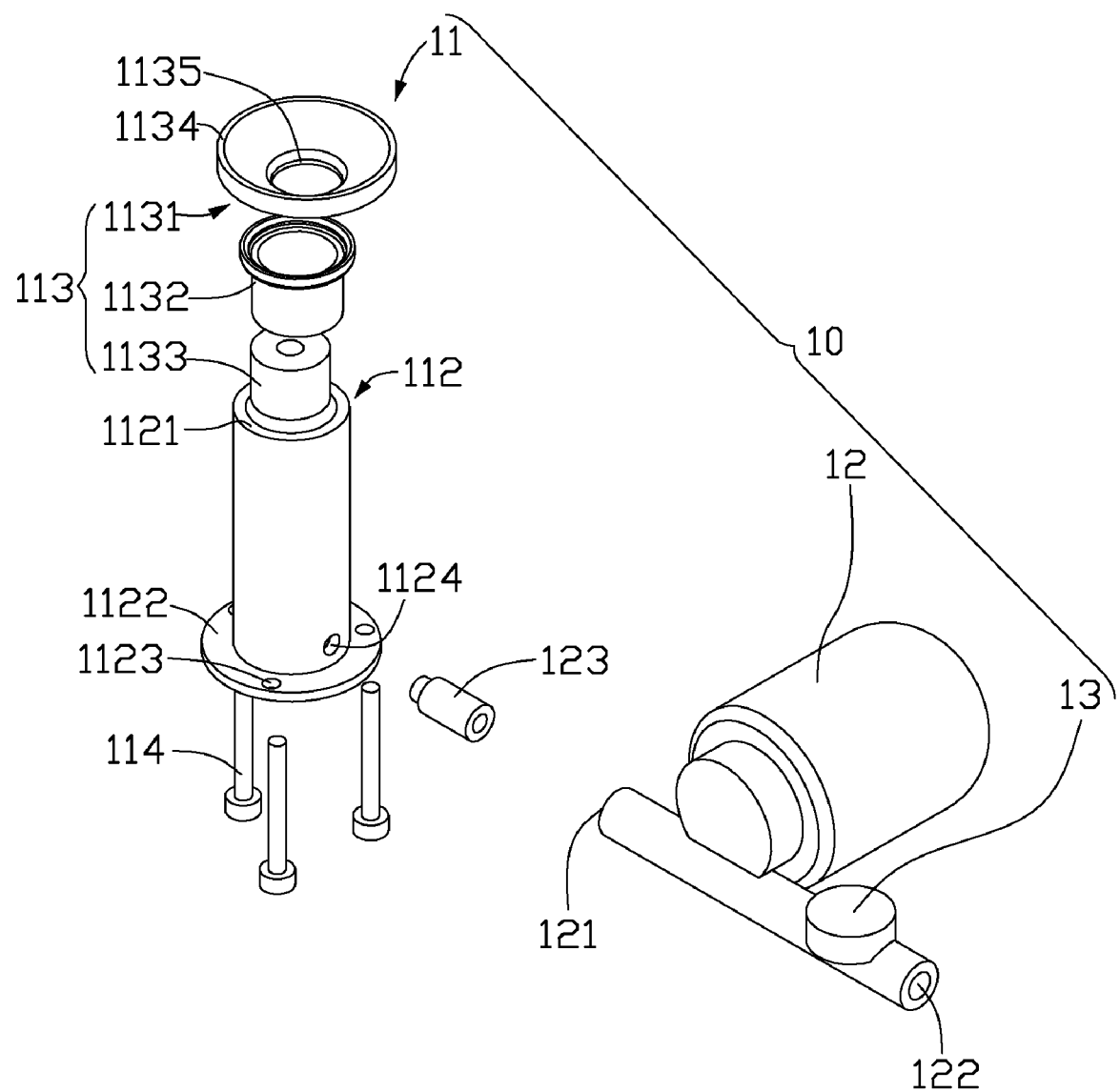
FIG. 2 is an exploded, enlarged, isometric view of a collecting device of the apparatus.
Figure 3:
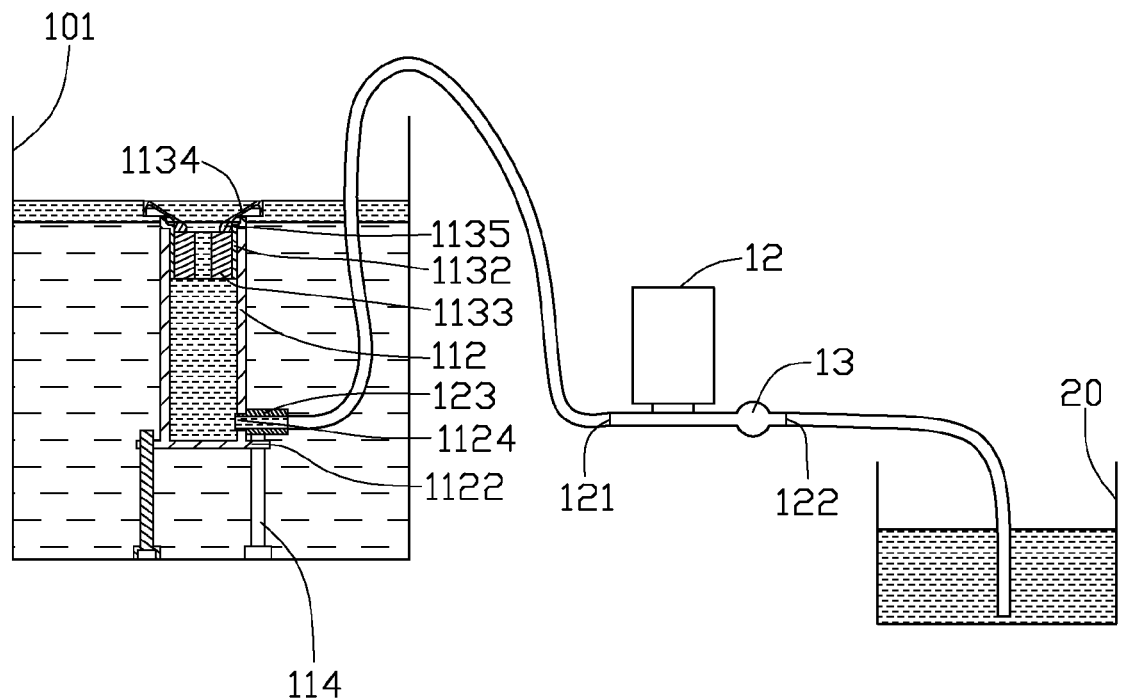
FIG. 3 is a cross-sectional, using view of the apparatus of FIG. 1.

Referring to FIGS. 2 and 3, the collecting device 10 includes a pollutant collecting structure 11, a bi-directional pump 12, and a controlling module 13. The pollutant collecting structure 11 connects to the bi-directional pump 12. The controlling module 13 is configured for controlling the bi-directional pump 12 to pump the liquid in a first direction or in a second direction opposite to the first direction.

The pollutant collecting structure 11 includes a hollow tub 112, a collecting module 113, and three adjusting members 114. The collecting module 113 is partially received in the hollow tub 112 and is slidable relative to the hollow tub 112.

The hollow tub 112 includes a main portion 1121 and a platform base 1122 connecting to one end of the main portion 1121. The platform base 1122 defines a plurality of threaded holes 1123. The number of the threaded holes 1123 is preferably three. The main portion 1121 is cylindrical and defines a through hole 1124 adjacent to the platform base 1122.

The collecting module 113 includes a skimming member 1131, a skimmer supporting cup 1132, and a floating platform 1133. The skimming member 1131 is a funnel-shaped member including a skimming portion 1134 and a mounting portion 1135 connecting to the skimming portion 1134. The mounting portion 1135 of the skimming member 1131 is attached in a top cavity defined in a top end of the skimmer supporting cup 1132. The skimmer supporting cup 1132 is substantially cylindrical. The floating platform 1133 is a hollow cylinder made of a solid buoyancy material (SBM) such as foam polystyrene, and so on. The floating platform 1133 is received in a bottom cavity defined in a bottom end of the skimmer supporting cup 1132. The floating platform 1133 is able to float in the hollow tube 112 when the hollow tube 112 is filled with liquid, thereby supporting the skimmer supporting cup 1132 that is supporting the skimming member 1131.

The adjusting members 114 are screws. The adjusting members 114 are configured to engage in the threaded holes 1123 of the platform base 1122 so that a height of the apparatus 10 can be adjusted.

It should be pointed out that, the skimming member 1131 and the skimmer supporting cup 1132 can be integrally made. The skimmer supporting cup 1132 and the floating platform 1133 are not limited to cylindrical, they can also be other shapes, such as quadrangular prism.

In use, the pollutant collecting structure 11 is placed in the coolant tank 101. Because the floating platform 1133 is made of solid buoyancy material, the skimming member 1131 floats in a body of a liquid having oil and/or coolant in the tub 112 thus vertically displacing the skimming member 1131. The skimming portion 1134 of the skimming member 1131 is preferably displaced to a position below the interface between the oil and the coolant. In addition, because the collecting module 113 is slidable relative to the hollow tub 112, a position of the collecting module 113 can be adjusted. Therefore, the apparatus 10 has high efficiency for removing buoyant pollutants such as oil and debris floating atop the body of the polluted coolant. It should be pointed out that, in order to entirely remove the oil and debris buoyant pollutants, the liquid removed by the apparatus 10 includes some coolant.

The bi-directional pump 12 is a solenoid pump. The bi-directional pump 12 includes an input portion and an output portion communicating with the input portion. The input portion defines an input hole 121 and the output portion defines an output hole 122. The input hole 121 is connected to the through hole 1124 of the hollow tub 112 by a flexible tube (not labeled). The output hole 122 is connected to a container 20 by another flexible tube (not labeled). The pump 12 pumps the liquid in the first direction in a pollutant removing state. The flexible tube connects to the through hole 1124 with a fixing member 123.

Referring to FIG. 3, the controlling module 13 connects to the bi-directional pump 12 for controlling the bi-directional pump 12 to pumps the liquid in the first direction or in the second direction according to a pressure of a liquid of the coolant and/or the oil. The controlling module 13 is preferably a pressure switch. The controlling module 13 is configured to detect the liquid pressure in the bi-directional pump 12. When the bi-directional pump 12 is enabled, the bi-directional pump 12 pumps the liquid in the first direction, thereby pumping the liquid out of the hollow tub 112, through the tubes and flews into the removing device 20. The bi-directional pump 12 continues to pump the liquid in the first direction for a predetermined period of time, for example, two minutes. If the liquid pressure detected by the controlling module 13 is in a normal range, the bi-directional pump 12 continues to pump the liquid in the first direction. If the through hole 1124 is clogged by debris of the buoyant pollutants, or when there is not enough liquid for the pump to create enough liquid pressure, the liquid pressure detected by the controlling module 13 decrease rapidly. When the liquid pressure decreases rapidly, the controlling module 13 control the bi-directional pump 12 to pump the liquid in the second direction. When the bi-directional pump 12 pump the liquid in the second direction, the liquid in the removing device 20 is pumped into the hollow tub 112 from the through hole 1124 of the hollow tub 112 and the impurities adjacent to the through hole 1124 can be broken into pieces and spitted out of the hollow tub 112. When the bi-directional pump 12 pumps the liquid in the second direction for a predetermined period of time, for example, two minutes, the controlling module 13 controls the pump 12 to pump the liquid in the first direction. After a predetermined period of time, the controlling module 13 decides whether the pump 12 should continue to pump the liquid in the first direction or not according to the detected liquid pressure. Therefore, the collecting device 10 is less likely to be clogged by impurities for a long time.

In an alternative embodiment, the controlling module 13 includes an electromagnetic valve (not shown) and a pressure sensor (not shown). The bi-directional pump 12 is replaced by a mono-directional pump. An input hole of the pump is connected to the electromagnetic valve by a first flexible tube, an output hole of the pump is connected to the electromagnetic valve by a second flexible tube, an input tube and an output tube are also connected to the electromagnetic valve. The input tube communicates with the hollow tub 112 of the pollutant collecting structure 11 and the output tube communicates with the removing device 20. The pressure sensor communicates with the pump for detecting the pressure of the liquid in the pump. The electromagnetic valve includes two working states and the working states can be exchanged according to the pressure of the liquid in the pump detected by the pressure sensor. In a first working state, the input tube communicates with the first flexible tube of the pump in the electromagnetic valve, and the output tube communicates with the second flexible tube in the electromagnetic valve. Thus, the pump can pump the liquid from the pollutant collecting structure 11 into the removing device 20 in the first working state. In a second working state, the input tube communicates with the second flexible tube of the pump in the electromagnetic valve, and the output tube communicates with the first flexible tube in the electromagnetic valve. Thus, the pump can pump liquid from the removing device 20 into the pollutant collecting structure 11 in the second working state.

If the pressure of the liquid in the pump detected by the pressure sensor is in a normal range, the electromagnetic valve continues/remains working in the first state so that the pump pumps liquid from the pollutant collecting structure 11 into the removing device 20. If the pressure of the liquid in the pump detected by the pressure sensor is in an abnormal range, that is, the through hole 1124 of the hollow tub 112 is clogged by impurities, the electromagnetic valve will turn to the second working state. The pump can pump liquid from the removing device 20 into the pollutant collecting structure 11 to crush the impurities adjacent to the through hole 1124 into pieces and spitted out of the hollow tub 112.

Referring to FIG. 1 again, the removing apparatus 20 includes a filter 21, and a pollutant removing structure 22. The pollutant removing structure 22 is positioned on the filter 21.

Figure 4:
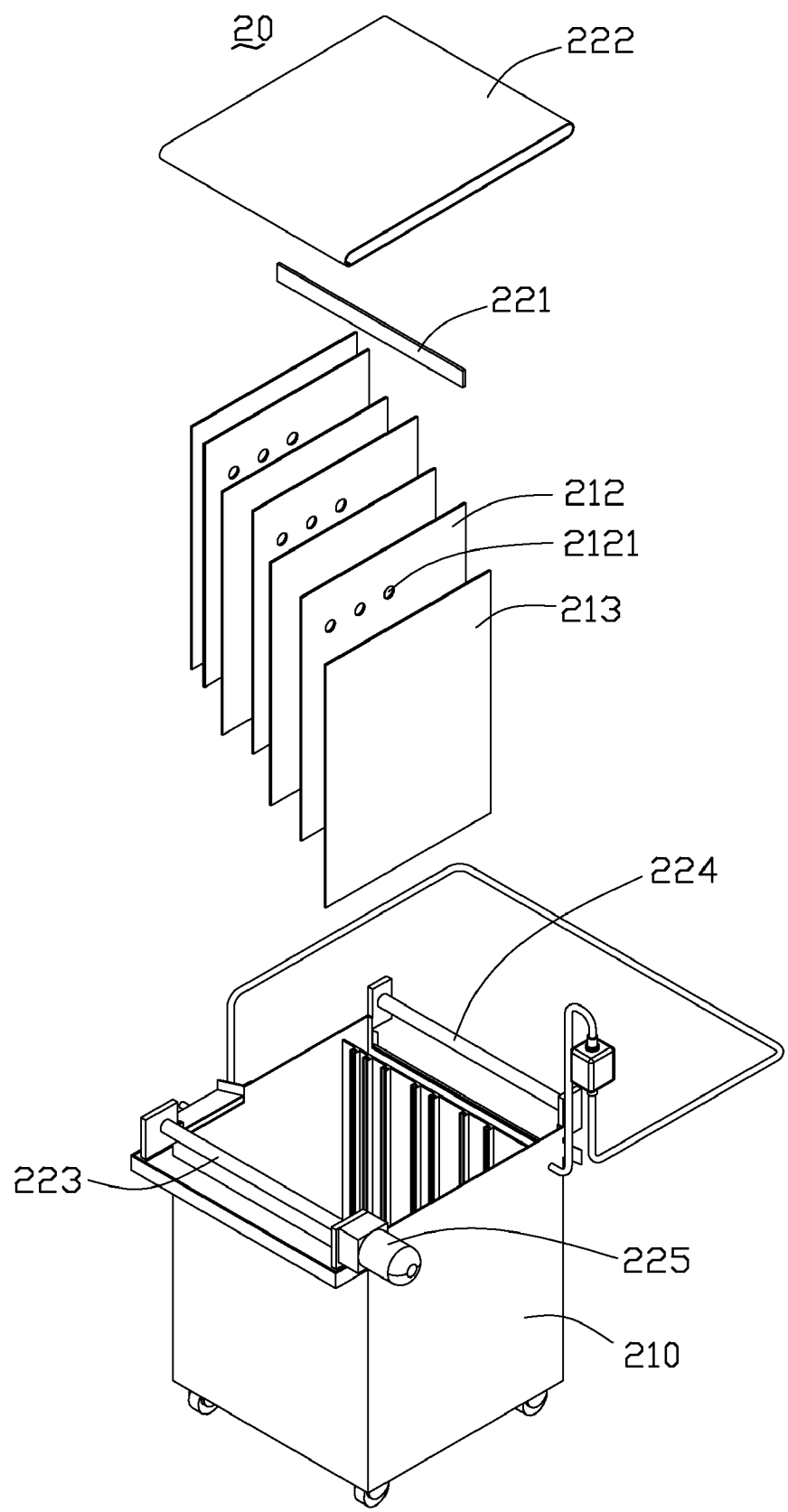
FIG. 4 is a partially exploded, isometric view of a removing device of the apparatus of FIG. 1.
Figure 6:
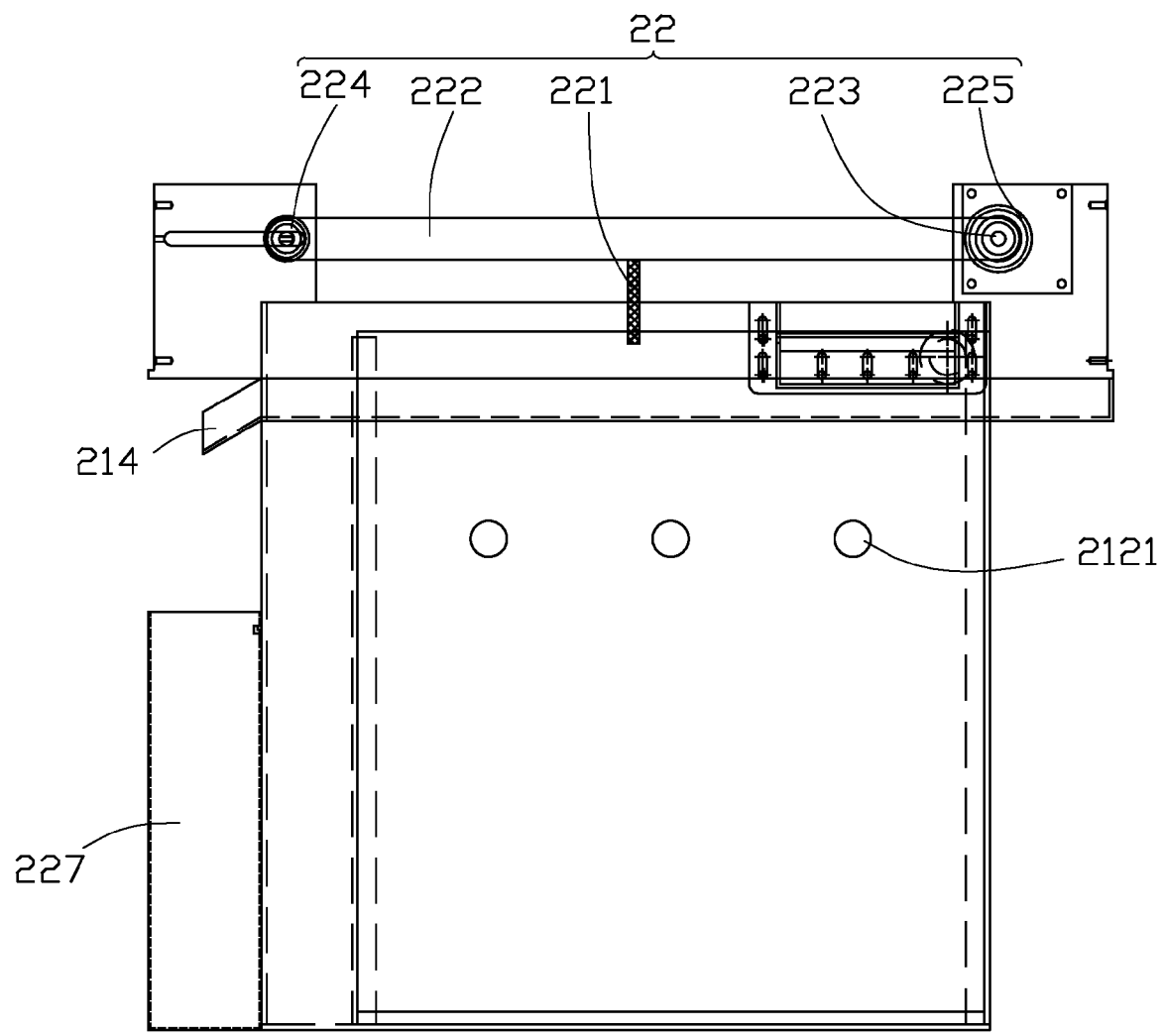
FIG. 6 is a front view of the removing device of FIG. 4.
Figure 7:
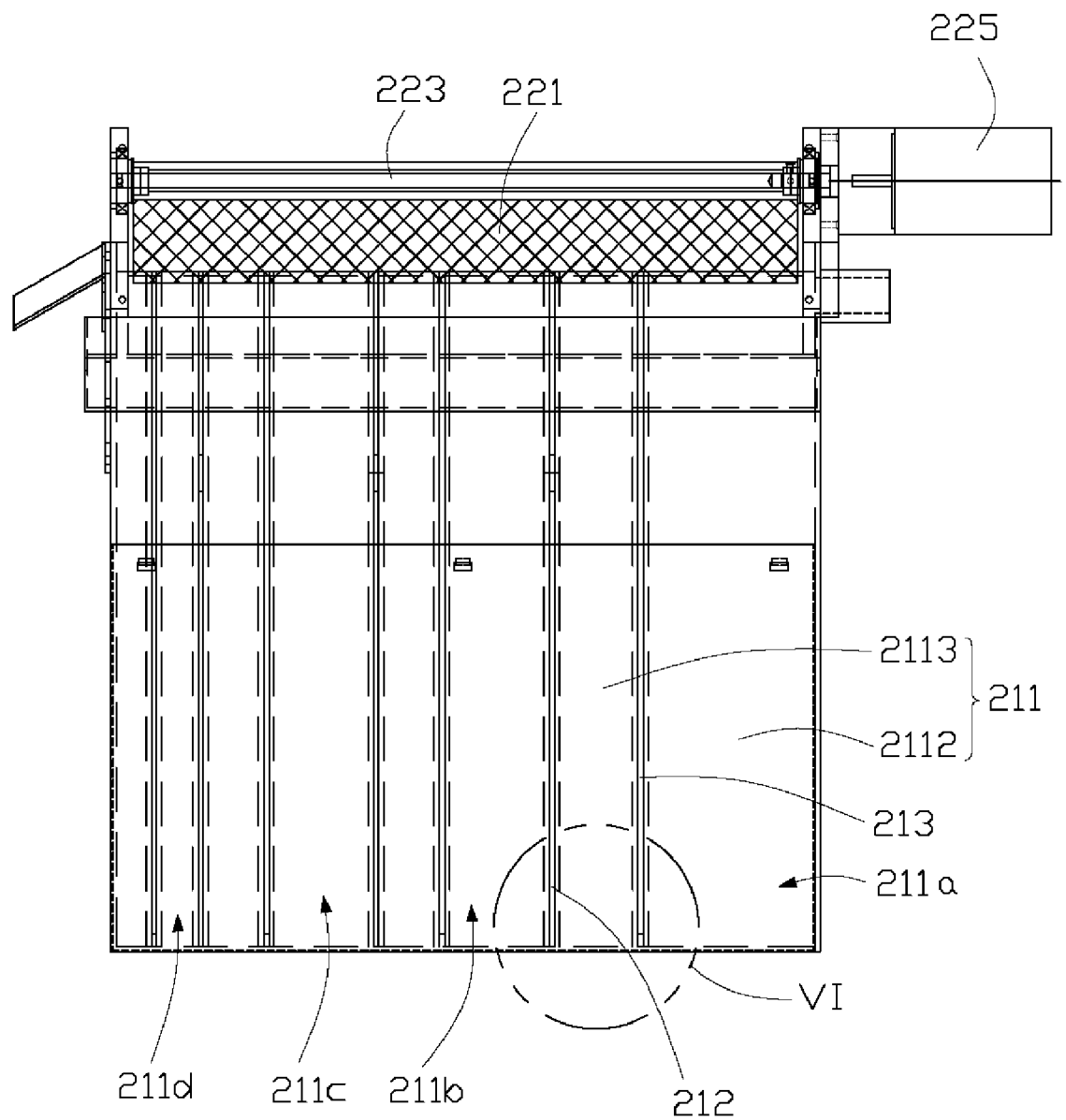
FIG. 7 is a side view of the removing device of FIG. 4.

Referring to FIGS. 4 and 7, the filter 21 includes a housing 210, a plurality of partition plates 212, and a plurality of partition sheets 213. The partition plates 212 and the partition sheets 213 are positioned in the housing 210 in an alternating manner, thereby forming a plurality of filtering units 211 that remove the buoyant pollutants from the polluted coolant. The number of the filtering units 211 is preferably four, that is, the filtering units 211 include a first filtering unit 211a, a second filtering unit 211b, a third filtering unit 211c, and a fourth filtering unit 211d. Adjacent filtering units 211 are partially separated by the partition plates 212 correspondingly. Each of the partition plates 212 defines a plurality of through holes 2121 adjacent to a top portion of the partition plate 212. The through holes 2121 are configured for adjacent filtering units 211 to communicate with each other. Referring to FIG. 6, each of the filtering units 211 is further separated into a first cavity 2112 and a second cavity 2113 by the partition sheets 213 correspondingly. Each of the partition sheets 213 is spaced apart from a bottom surface 2101 of the housing 210, thereby defining a communicating gap 2131 for the first cavity 2112 and the second cavity 2113 to communicate with each other.

In use, the pump 12 of the collecting device 10 pumps the polluted coolant into the first cavity 2112 of the first filtering unit 211a. Because liquid pollutants such as the oil float on the coolant, when the coolant flows into the second cavity 2113 through the communicating gap 2131, the liquid pollutants are mostly filtered out by the partition sheet 213 of the first filtering unit 211a. Thus the liquid pollutants are mostly separated from the coolant by the first filtering unit 211a. When the coolant in the second cavity 2113 reaches the through holes 2121 of the partition plate 212, the coolant flows into the first cavity 2112 of the second filtering unit 211b. Because solid pollutants such as the debris have a larger density than that of the coolant, the solid pollutants are easily mixed into the coolant by the pump 23, thus most of the solid pollutants sink to the bottom surface 2101 (shown in FIG. 8) of the first filtering unit 211a due to gravity, and unable to pass through the through holes 2121 of the partition plate 212. The remaining pollutants in the second filtering unit 211b are further separated from the coolant by the second filtering unit 211b. In a similar principle, the coolant is further filtrated by the remaining filtering units 211 (the third filtering unit 211c and the fourth filtering unit 211d), thus yielding filtrated coolant. The pollutants separated from the coolant mostly remain in the first cavity 2112 of the first filtering unit. An amount of the pollutants separated from the coolant gradually decreases from the first filtering unit 211a to the fourth filtering unit 211d. Therefore, the filtrated coolant in the second cavity 2113 of the fourth filtering unit 211d contains almost no buoyant pollutants and the filtrated coolant can be reused for cooling a cutting tool.

It should be pointed out that, the number of the filtering units 211 can also be at least one. When the amount of the filtering units 211 is only one, the partition plate 212 is accordingly omitted.

Figure 8:
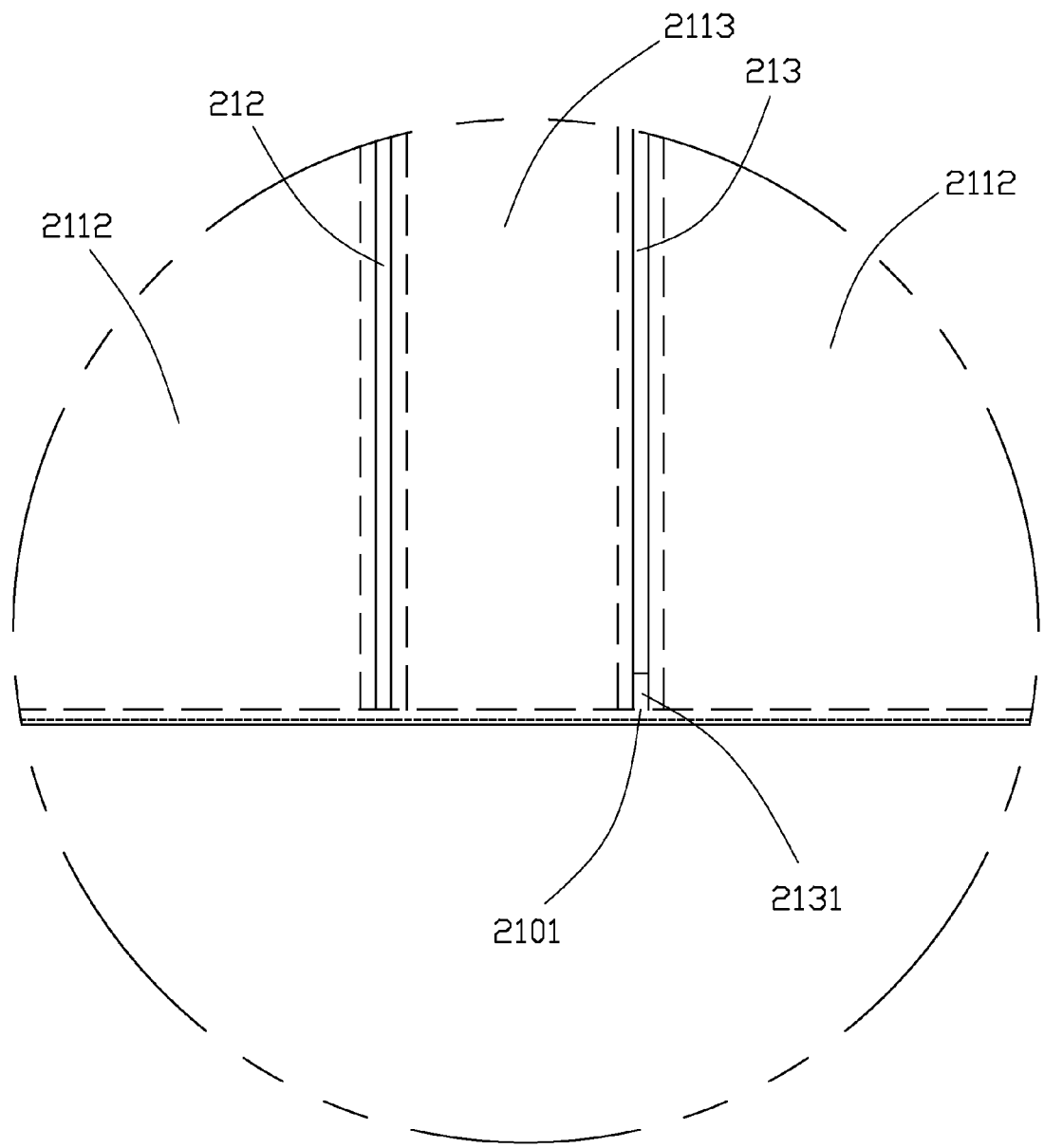
FIG. 8 is an enlarged view of a circled portion IX-IX of FIG. 7.

Referring to FIGS. 7 and 8, a top portion of the second cavity 2113 of the fourth filtering unit defines a coolant guiding groove 214 so that the filtrated coolant can flow into a coolant container (not shown) via the coolant guiding groove 214.

The pollutant removing structure 22 includes a removing member 221, a conveyer belt 222, a driver 223, a driven wheel 224, and a motor 225. The removing member 221 is a metallic piece or a brush fixed to the conveyer belt 222. The conveyer belt 222 is looped around the driver 223 and the driven wheel 224. The motor 225 is configured for driving the driver 223 so that the conveyer belt 222 rotates around the driver 223 and the driven wheel 224.

Figure 5:
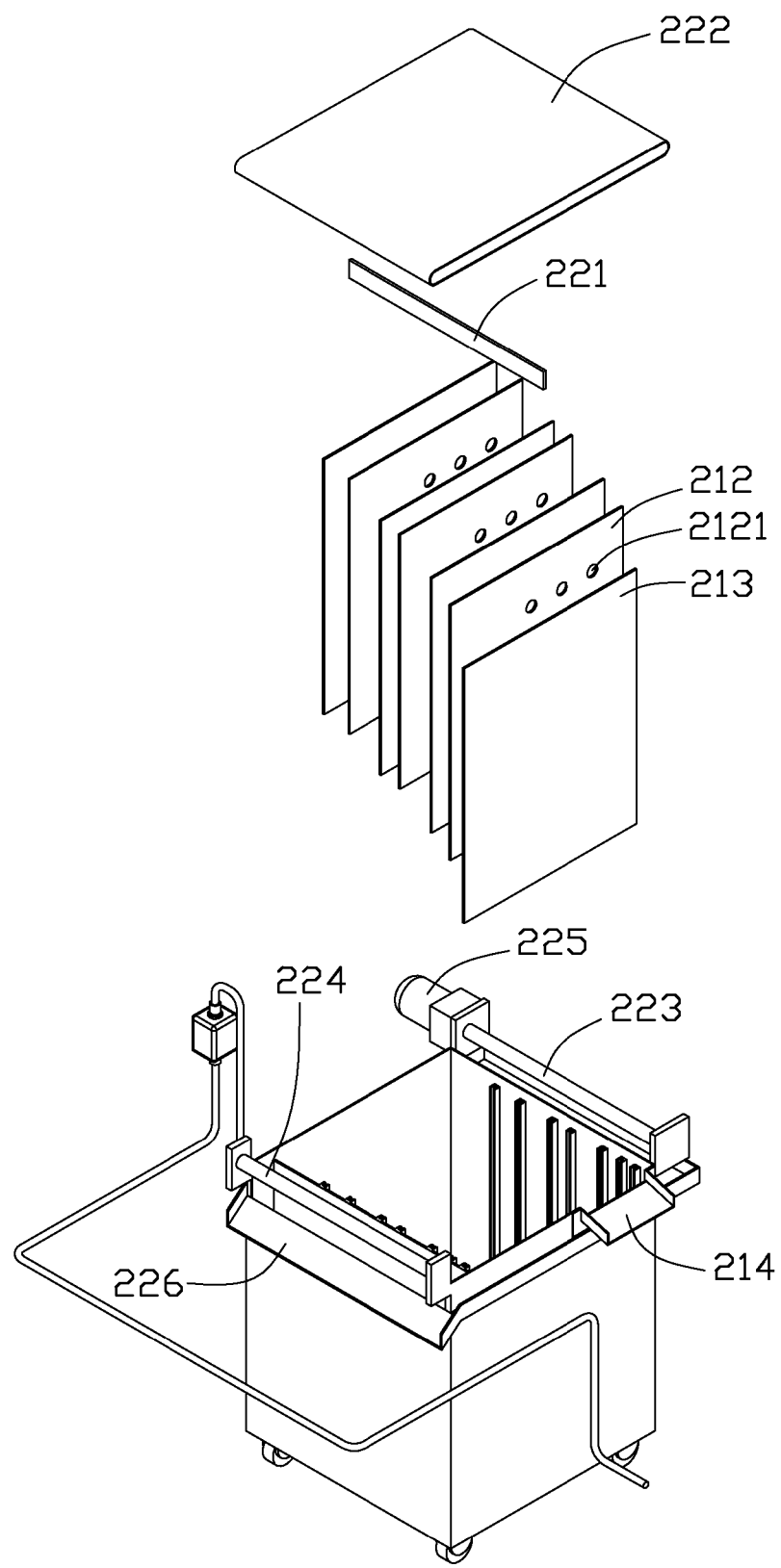
FIG. 5 is similar to FIG. 4, but viewed from another aspect.

It should be pointed out that, in FIG. 5, one end of the pollutant removing structure 22 defines a pollutant exit 226. In FIG. 6, a receiving case 227 is positioned below the pollutant exit 226, and the buoyant pollutants can be pushed out from the filtering units 211 via the pollutant exit 226 and flow into the receiving case 227.

To use the pollutant removing structure 22, an end of the removing member 221 is embedded below a surface of the floating buoyant pollutants. When the conveyer belt 222 is moved with the removing member 221, the removing member 221 sweeps the buoyant pollutants into the receiving case 227 from the pollutant exit 226. The removing member 221 directly pushes the buoyant pollutants from the coolant into the receiving case 227, thereby greatly increasing the efficiency for removing the buoyant pollutants.

It should be pointed out that, the pollutant removing structure 22 can be replaced by other structures, e.g., a reciprocating motion structure to drive the removing member 22 to move back and forth alternately. When the removing member 22 moves back and forth alternately, the removing member 221 directly pushes the buoyant pollutants from the coolant into the receiving case 227.

Referring again to FIG. 1, the bactericidal device 30 includes a liquefied gas pump 31 and an ozone generator 32 connects to the liquefied gas pump 31. The liquefied gas pump 31 connects to the coolant tank 101 by using an input tube (not shown) and an output tube (not shown). In use, the liquefied gas pump 31 pump coolant in the coolant tank 101 using the input tube, and the ozone generator 32 generates ozone into the liquefied gas pump 31. The liquefied gas pump 31 pumps the coolant for mixing the ozone and the coolant sufficiently, thus the micro-organisms in the coolant can be killed by the coolant. The coolant processed by the bactericidal device 30 flews into the coolant tank 101 from the output tub. Therefore, the bactericidal device 30 further increases the usage life of the coolant.

It is believed that the present embodiments and their advantages will be understood from the foregoing description, and it will be apparent that various changes may be made thereto without departing from the spirit and scope of the invention or sacrificing all of its material advantages, the examples hereinbefore described merely being preferred or exemplary embodiments of the invention.

What is claimed is:

1. An apparatus, for removing buoyant pollutants from a polluted coolant, the apparatus comprising:

a collecting device including a pollutant collecting structure and a bi-directional pump, the pollutant collecting structure including a hollow tub and a collecting module, the collecting module being partially received in the hollow tub and slidable relative to the hollow tub, the bi-directional pump communicating with the hollow tub; and a removing device communicating with the bi-directional pump, the removing device including a filter and a pollutant removing structure disposed on the filter, the filter including at least one filtrating unit for removing the buoyant pollutants from the polluted coolant, the filtrating unit being partitioned into a first cavity and a second cavity by a partition sheet, the partition sheet being spaced apart from a bottom surface of the filter to define a communicating gap for the first cavity and the second cavity to communicate with each other, and the pollutant removing structure including a removing member for removing the buoyant pollutants out of the filter.

2. The apparatus as claimed in claim 1, further comprising a bactericidal device having a liquefied gas pump for pumping the coolant and an ozone generator connecting to the liquefied gas pump for generating ozone into the liquefied gas pump.

3. The apparatus as claimed in claim 1, further comprising a controlling module for controlling the bi-directional pump to pump a liquid having the buoyant pollutants and the polluted coolant into the hollow tub or out of the hollow tub.

4. The apparatus as claimed in claim 3, wherein the controlling module is a pressure switch connecting to the bi-directional pump for controlling the bi-directional pump to pump the liquid in a first direction or in a second direction opposite to the first direction according to a pressure of the liquid in the bi-directional pump.

5. The apparatus as claimed in claim 1, wherein the hollow tub comprises a main portion and a platform base connecting to one end of the collecting sleeve, the main portion defines a through hole adjacent to the platform base, and the through hole communicates with an input hole of the bi-directional pump.

6. The apparatus as claimed in claim 5, wherein the main portion is cylindrical.

7. The apparatus as claimed in claim 5, wherein the platform base includes a plurality of threaded holes defined therein, the removing device includes a plurality of adjusting members for engaging in the threaded holes of the platform base so that a height of the apparatus can be adjusted.

8. The apparatus as claimed in claim 5, wherein the platform base includes three threaded holes defined therein, and the removing device includes three screws for engaging in the threaded holes of the platform base so that a height of the apparatus can be adjusted.

9. The apparatus as claimed in claim 1, wherein the collecting module comprises a skimming member, a skimmer supporting cup, and a floating platform; and one end of the skimming member is attached in a top end the skimmer supporting cup, the floating platform is received in a bottom end of the skimmer supporting cup.

10. The apparatus as claimed in claim 9, wherein the skimming member is a funneled member, the skimming member includes a skimming portion and a mounting portion connecting to the skimming portion; and the sleeve is cylindrical and the top end of the sleeve engages with the mounting portion.

11. The apparatus as claimed in claim 9, wherein the floating platform is a hollow cylinder made of a solid buoyancy material.

12. The apparatus as claimed in claim 11, wherein the solid buoyancy material is foam polystyrene.

13. The apparatus as claimed in claim 1, wherein the bi-directional pump is a solenoid pump.

14. The apparatus as claimed in claim 1, wherein the pollutant removing structure comprises a removing member, a conveyer belt, a driver, a driven wheel, and a motor, the removing member is fixed to the conveyer belt, the conveyer belt surrounds the driver and the driven wheel, and the motor is configured for driving the driver so that the conveyer belt can be moved.

15. The apparatus as claimed in claim 1, wherein the filter comprises a housing, a plurality of partition plates, and a plurality of partition sheets, the partition plates and the partition sheet are positioned in the housing in an alternating manner to form a plurality of filtering units, adjacent filtering units being separated by the partition plates correspondingly, each of the partition plate defining a plurality of through holes adjacent to an top portion thereof for adjacent filtering units to communicate with each other.

16. The apparatus as claimed in claim 1, wherein one end of the pollutant removing structure defines a pollutant exit, and a receiving case is disposed below the pollutant exit for receiving the buoyant pollutants.

17. The apparatus as claimed in claim 1, wherein the removing member is a metallic piece.

18. The apparatus as claimed in claim 1, wherein the removing member is a brush.

* * * * *